(12) United States Patent
Haug et al.

(10) Patent No.: US 9,539,205 B2
(45) Date of Patent: Jan. 10, 2017

(54) EMULSION

(75) Inventors: Ingvild Haug, Trondheim (NO); Kurt Ingar Draget, Trondheim (NO)

(73) Assignee: AYANDA GROUP AS, Oslo (NO)

( * ) Notice: Subject to any disclaimer, the term of this patent is extended or adjusted under 35 U.S.C. 154(b) by 536 days.

(21) Appl. No.: 12/162,339

(22) PCT Filed: Jan. 25, 2007

(86) PCT No.: PCT/GB2007/000261
§ 371 (c)(1),
(2), (4) Date: May 1, 2009

(87) PCT Pub. No.: WO2007/085840
PCT Pub. Date: Aug. 2, 2007

(65) Prior Publication Data
US 2009/0220576 A1    Sep. 3, 2009

(51) Int. Cl.
| | | |
|---|---|---|
| *A61K 9/00* | (2006.01) |
| *A23G 4/06* | (2006.01) |
| *A61K 9/107* | (2006.01) |
| *A61K 47/26* | (2006.01) |
| *A61K 47/36* | (2006.01) |
| *A61K 47/42* | (2006.01) |
| *A61K 47/44* | (2006.01) |

(52) U.S. Cl.
CPC .......... *A61K 9/0056* (2013.01); *A23G 4/066* (2013.01); *A23L 29/281* (2016.08); *A23L 33/115* (2016.08); *A61K 9/107* (2013.01); *A61K 47/26* (2013.01); *A61K 47/36* (2013.01); *A61K 47/42* (2013.01); *A61K 47/44* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,695,450 A | 9/1987 | Bauer et al. | |
| 4,764,383 A | 8/1988 | Brown et al. | |
| 4,935,243 A | 6/1990 | Borkan et al. | |
| 4,961,939 A * | 10/1990 | Antrim et al. | 426/61 |
| 5,549,204 A * | 8/1996 | Toren | 206/539 |
| 2003/0068407 A1 | 4/2003 | Chiavazza et al. | |
| 2004/0001873 A1* | 1/2004 | Base et al. | 424/439 |
| 2004/0121000 A1 | 6/2004 | Bowe et al. | |
| 2006/0088645 A1 | 4/2006 | Nietling et al. | |

FOREIGN PATENT DOCUMENTS

| | | |
|---|---|---|
| EP | 0 474 261 A2 | 3/1992 |
| EP | 1782807 A1 | 5/2007 |
| GB | 2 086 835 A | 5/1982 |
| JP | 5238954 A | 9/1993 |
| JP | 09-224578 | 9/1997 |
| JP | 11-056245 | 3/1999 |
| JP | 11-056315 | 3/1999 |
| JP | 2000-279107 | 10/2000 |
| JP | 2004-520355 A | 7/2004 |
| JP | 2004-238419 A | 8/2004 |
| JP | 2005-500157 | 1/2005 |
| JP | 2005-512552 A | 5/2005 |
| JP | 2006-115831 A | 5/2006 |
| JP | 4943849 B2 | 5/2012 |
| WO | WO 03/018186 A1 | 3/2003 |
| WO | WO 03/053159 A1 | 7/2003 |
| WO | WO 2004/054539 A1 | 7/2004 |
| WO | WO 2005/105290 A1 | 11/2005 |

* cited by examiner

*Primary Examiner* — Patricia Duffy
*Assistant Examiner* — Garen Gotfredson
(74) *Attorney, Agent, or Firm* — Knobbe, Martens Olson & Bear, LLP

(57) ABSTRACT

The invention relates to an orally administrable chewable composition in unit dosage form comprising an oil-in-water emulsion in which the aqueous phase is gelled and in which the oil phase comprises a physiologically tolerable unsaturated fatty acid ester.

12 Claims, No Drawings

EMULSION

This application is U.S. National Phase of International Application PCT/GB2007/000261, filed Jan. 25, 2007 designating the U.S., and published in English as WO2007/085840 on Aug. 2, 2007, which claims priority to Great Britain Patent Application No. 0601498.9 filed Jan. 25, 2006.

FIELD OF THE INVENTION

This invention relates to compositions for oral administration in the form of chewable emulsions containing physiologically tolerable unsaturated fatty acid ester oils.

BACKGROUND OF THE INVENTION

The term unsaturated fatty acid ester oil is used herein to relate to acyl glycerides and phospholipids, i.e. compounds comprising an unsaturated fatty acid side chain linked by an ester group to an "alcohol" (e.g. polyol) residue. Such compounds are important dietary sources of fatty acids, in particular polyunsaturated fatty acids (PUFAs) and more especially the essential fatty acids. They may also serve as sources for dietary replacements of essential fatty acids, e.g. of conjugated linoleic acid (CLA) which may be used in a weight reduction diet. Particularly important essential fatty acids include the $\omega$-3, $\omega$-6 and $\omega$-9 acids such as eicosapentaenoic acid (EPA) and docosahexaenoic acid (DHA). Other fatty acids commonly used in nutraceuticals and pharmaceuticals include arachidonic acid (AA), alpha linolenic acid (ALA), conjugated linolenic acid (CLN), dihomo-gamma linolenic acid (DGLA) and gamma linolenic acid (GLA). Such fatty acids typically will contain 12 to 26 carbons, more typically 16 to 22 carbons, and will have a saturated or mono- or poly-ethylenically-unsaturated hydrocarbyl chain.

Typical dietary sources of such fatty acid ester oils include lipids such as animal, fish, plant or microorganism triglycerides and phospholipids, especially the triglycerides. Mono or diglycerides however can equally be used as can other esters, e.g. lower alkyl (e.g. $C_{1-6}$ alkyl, for example ethyl) esters as well as free fatty acids or physiologically acceptable salts thereof and fatty acid ester waxes. Particularly important sources are fish oils, in particular oily fish oils such as cod-liver oil, halibut-liver oil, etc. as these are rich in $\omega$-3, $\omega$-6 and $\omega$-9 fatty acids.

However, as anyone who, in childhood, has been on the receiving end of fish oils will recall, the taste, mouthfeel and smell can be vile. In part this is due to the sensitivity to oxidation of the fish oil. As a result fatty acid ester oils tend to be administered in capsule form, containing liquid oil within a soft gel casing. Such capsule casings are usually made from mammalian gelatin, typically of porcine or bovine origin. In order to deliver a reasonable dose of the oil, the capsules tend to be rather large, sufficiently large indeed to cause problems swallowing them for the young and the elderly. As a result, ingestion often involves the capsule being chewed and bursting in the mouth releasing the unpleasantly tasting oil contents.

There is thus a continuing need for improved oral administration forms for unsaturated fatty acid ester oils.

We have now surprisingly found that chewable set emulsions of unsaturated fatty acid esters remain sufficiently free of bad odour and taste.

DETAILED DESCRIPTION OF THE PREFERRED EMBODIMENT

Thus viewed from one aspect the invention provides an orally administrable chewable composition in unit dosage form comprising an oil-in-water emulsion in which the aqueous phase is gelled and in which the oil phase comprises a physiologically tolerable unsaturated fatty acid ester.

The term "chewable" is used herein in its conventional meaning within the pharmaceutical and nutraceutical industry. That is the composition is in a form which can be broken or fragmented by chewing.

The chewable compositions of the invention may be pharmaceuticals, but preferably are nutraceuticals.

The oil phase of the emulsion will typically comprise a physiologically tolerable unsaturated fatty acid ester oil as described above, especially an acyl glyceride or a fatty acid ethyl ester, and in particular a fish or plant triglyceride. More preferably, it contains a fish oil. Besides such oils, or mixtures thereof, the oil phase may also if desired contain physiologically tolerable lipid soluble materials, e.g. vitamins, antioxidants, flavourings, colours and other physiologically active materials. If desired, the oil phase may be constituted in whole or part by a phospholipid, in particular a marine (eg pelagic fish or shellfish, for example krill) phospholipid. The oil phase preferably contains 25 to 100% of the recommended daily dosage for one or more essential fatty acids, especially EPA and/or DHA. Typically the oil phase will constitute 0.05 to 5 g, preferably 0.1 to 3 g, especially 0.2 to 2 g, particularly 0.3 to 1.25 g, more particularly 0.4 to 0.75 g, per dose unit. Alternatively put, the oil phase preferably constitutes 5 to 75% wt., especially 30 to 50% wt., eg 40 to 50% wt. of the dose unit.

The aqueous phase of the emulsion comprises water and a physiologically tolerable gelling agent, preferably a saccharide (e.g. an oligosaccharide or polysaccharide), a protein or a glycoprotein. Suitable gelling agents are well known in the food, pharmaceutical and nutraceutical industries and several are described for example in Phillips et al. (Ed.) "Handbook of hydrocolloids", Woodhead Publishing, Cambridge, UK, 2000. The gelling agents are preferably materials capable of undergoing a sol-gel transformation, e.g. under the influence of a change in physiochemical parameters such as temperature, pH, presence of metal ions (e.g. group 1 or 2 metal ions), etc.

Preferred for use as the gelling agent is gelatin or a mixture of gelatin and a polysaccharide, or gellan, or an alginate (eg sodium alginate), or a mixture of an alginate and glucono-delta-lactone (GDL). The use of fish gelatins is especially preferred.

The gelatins used as gelling agents in the composition of the invention may be produced from the collagen of any mammal or the collagen of any aquatic species, however the use of gelatin from salt-water fish and in particular cold water fish is preferred. Gelatins having an imino acid content of 5 to 25% wt. are preferred, more especially those having an imino acid content of 10 to 25% wt. The gelatins will typically have a weight average molecular weight in the range 10 to 250 kDa, preferably 75 to 220 kDa, especially 80 to 200 kDa. Gelatins having Bloom values of 60-300, especially 90-200 are preferred. The gelatin will typically be present in the aqueous phase at a concentration of 1 to 50% wt., preferably 2 to 35% wt., particularly 5 to 25% wt. In the case of mixtures of gelatin and polysaccharides, the weight ratio of gelatin to polysaccharide in the aqueous phase will typically be 50:1 to 5:1, preferably 40:1 to 9:1, especially 20:1 to 10:1.

Where polysaccharides, or mixtures of polysaccharides and gelatin are used as the gelling agent, it is preferred to use natural polysaccharides, synthetic polysaccharides or semi-synthetic polysaccharides, e.g. polysaccharides from plants, fish, terrestrial mammals, algae, bacteria and derivatives and fragmentation products thereof. Typical marine polysaccharides include carageenans, alginates, agars and chitosans. Typical plant polysaccharides include pectins. Typical microorganism polysaccharides include gellans and scleroglucans. The use of charged, e.g. electrostatically charged and/or sulphated polysaccharides is preferred, as is the use of marine polysaccharides, in particular carageenans, and alginates, especially carageenans. Carageenans are used below as representative polysaccharide gelling agents.

The carageenan family, which includes iota- and kappa-carageenans, is a family of linear sulphated polysaccharides produced from red algae. The repeating disaccharide unit in kappa-carrageenan is β-D-galactose-4-sulphate and 3,6-anhydro-α-D-galactose, while that in iota-carrageenan is β-D-galactose-4-sulphate and 3,6-anhydro-α-D-galactose-2-sulphate. Both kappa-and iota-carrageenans are used in food preparations. The carrageenans are used as stabilisers, emulsifiers, gelling agents and fat replacers.

Both iota and kappa carrageenans form salt- or cold-setting reversible gels in an aqueous environment. Coil-helix transition and aggregation of helices form the gel network. Kappa-carrageenan has binding sites for specific monovalent cations, resulting in gel formation with decreasing shear and elastic moduli in the order $Cs^+>K^+>>Na^+>Li^+$. As a rule, an increasing salt concentration enhances the elastic modulus and the setting and melting temperatures of a kappa-carrageenan gel. The use of water-soluble potassium, rubidium, or cesium compounds, particularly potassium compounds, and particularly naturally occurring compounds (e.g. salts) is preferred when kappa-carrageenan is used according to the invention, e.g. at concentrations of up to 100 mM, more especially up to 50 mM. A salt-dependent conformational transition is also found for iota-carrageenan. The molecules are also known to undergo coil-helix transition with strong helix-stabilisation in the presence of multivalent cations, like $Ca^{2+}$. The use of water-soluble calcium, strontium, barium, iron or aluminium compounds, especially calcium compounds, and particularly naturally occurring compounds (e.g. salts) is preferred when iota-carrageenan is used according to the invention, e.g. at concentrations of up to 100 mM.

The polysaccharide gelling agents used according to the invention will typically have weight average molecular weights of 5 kDa to 2 MDa, preferably 10 kDa to 1 MDa, most preferably 100 kDa to 900 kDa, particularly 400 to 800 kDa. They will typically be used at concentrations of 0.01 to 5% wt, preferably 0.1 to 1.5% wt., particularly 0.2 to 1% wt in the aqueous phase. Where mono or multivalent cations, typically group 1 or group 2 metal ions, are included in the aqueous phase, this will typically be at concentrations in the range 2.5 to 100 mM, particularly 5 to 50 mM.

Besides the gelling agent and water and any required gelling initiator, other physiologically tolerable materials may be present in the aqueous phase, e.g. emulsifiers, emulsion stabilisers, pH modifiers, viscosity modifiers, sweeteners, fillers, vitamins (e.g. vitamin C, thiamine, riboflavin, niacin, vitamin B6, vitamin B12, folacin, panthotenic acid), minerals, aromas, flavours, colours, physiologically active agents, etc. It is especially preferred that a lipophilic antioxidant, e.g. vitamin E, be included in the oil phase. Other vitamins which may be present in the oil phase are vitamin A, vitamin D and vitamin K. Such further components are used widely in the food, pharmaceutical and nutraceutical industries. The use of cellulose derivatives (e.g. hydroxy methyl propyl cellulose) as emulsion stabilizers is especially preferred.

The pH of the aqueous phase of the emulsion is preferably in the range 2 to 9, particularly 3 to 7.5.

The aqueous phase preferably has a gelling temperature in the range 10 to 30° C., more preferably 15 to 28° C., and a melting temperature in the range 20 to 80° C., more preferably 24 to 60° C., especially 28 to 50° C.

Where a sweetener is included in the aqueous phase, this will typically be selected from natural sweeteners such as sucrose, fructose, glucose, reduced glucose, maltose, xylitol, maltitol, sorbitol, mannitol, lactitol, isomalt, erythritol, polyglycitol, polyglucitol and glycerol and artificial sweeteners such as aspartame, acesulfame-K, neotame, saccharine, sucralose. The use of non-cariogenic sweeteners is preferred.

The emulsion preferably has an oil content of 1 to 90% wt, especially 5 to 80% wt, more especially 20 to 75% wt. However after emulsification and gelation the emulsion may be dried to reduce the water content, e.g. to 0.01 to 50% wt, preferably 0.1 to 40% wt, especially 0.5 to 30% wt. Particularly preferably however the aqueous phase, even after any drying step, will constitute at least 10% wt., more preferably at least 20% wt., especially at least 30% wt., particularly at least 40% wt. of the emulsion "residue". Where the emulsion is dried, e.g. by lyophilization, the discontinuous nature of the oil phase is maintained even though the water content of the emulsion residue may be extremely low. In general, however, where a dried gelled emulsion is used, it is preferred that it still contains a continuous gel network phase, e.g. as detectable by electron microscopy.

Examples of physiologically active agents that may be included in the capsules of the invention include for example analgesics (eg paracetamol and acetyl salicylic acid) and antihistamines.

Preferably the overall dose unit weight will be 0.25 to 3 g, especially 0.5 to 2.5 g, more especially 0.75 to 2 g.

Viewed from a further aspect the invention provides a method of treatment of a human by oral administration of an effective amount of an active agent in oil form or dissolved in an oil, the improvement comprising administering said active agent in a chewable emulsion according to the invention. The method may thus typically be a method of treatment of a disease or ailment (eg pain), a method of nutritional supplementation (eg with a triglyceride) or a method of reducing weight.

Emulsion formation may be effected by conventional techniques; however emulsification under a non-oxidising gas, eg nitrogen, is preferred. Likewise, the components of the emulsion are preferably degassed before emulsification and handling and packaging of the set emulsion is preferably performed under such a gas.

The dose units of the emulsion may be formed for example by moulding, extrusion or cutting or the like. For adult use, the dose units are preferably in tablet or lozenge form; however for child use they may conveniently be presented in child-friendly form, eg geometric shapes such as rods, strips and tubes, or animal, doll, or vehicle shapes, for example the shape of a popular cartoon character.

It is particularly preferred that the compositions according to the invention contain a citrus flavour (e.g. orange or lemon oil) in order to mask any remaining oil taste on chewing. It is also particularly preferred that the compositions according to the invention contain xylitol, e.g. as 0.5 to 50% wt., preferably 1 to 40% wt., eg 15 to 40% wt., in order to mask both taste and mouth feel. These may be in the aqueous phase or the oil phase (e.g. as a water-in-oil-in water emulsion), or both; however inclusion in the aqueous phase will generally be sufficient.

The dose units of the compositions of the invention are preferably individually packaged in air-tight containers, eg a sealed wrapper or more preferably a blister of a blister pack. Viewed from a further aspect the invention provides a package comprising an air-tight compartment containing one dose unit of a composition according to the invention.

The packages according to the invention are preferably in the form of blister packs containing at least two dose units, eg 2 to 100, preferably 6 to 30. A blister pack, as is well known, usually comprises a plastic sheet base having moulded indentations or trays in which the item to be packed is placed. The pack is normally sealed with a foil, generally metal or a metal/plastic laminate, generally by heating the areas between the indentations or trays.

The packages according to the invention are preferably filled under a non-oxidising gas atmosphere (eg nitrogen) or are flushed with such a gas before sealing.

Of course, in place of unsaturated fatty acid esters, saturated fatty acids and their esters could also be used and this forms a further aspect of the invention.

The invention will now be described further with reference to the following non-limiting Examples.

EXAMPLE 1

Chewable Emulsion
Aqueous Phase:
Gelatin: 10% wt.
Sorbitol: 50% wt.
Lemon flavour: 0.15% wt.
Yellow color: 0.1% wt.
Water: 100% wt.

The gelatin is added to the water and allowed to swell for 30 min. The gelatin solution is then heated to 60° C. under continuous stirring for 45 min. The sorbitol is then added to the solution and allowed to dissolve under stirring for 30-60 min. The flavour and color are then added while stirring. The solution is mixed for 30 min before stirring is stopped and the solution is left for 30 min. The resultant solution is degassed under vacuum to remove air bubbles. 0.02% wt. lecithin is added to this solution.

Marine oil (e.g. commercially available fish liver oil) is mixed with 0.15% wt. lemon flavour.

The marine oil and the aqueous solution are emulsified in a weight ratio of 1:2 at 45-50° C. using an ultra turrax. When the emulsion is smooth, soft cores are produced by moulding and left to gel for 30 min at 22° C. The cores are dried to reduce the content of water to approximately 15% wt.

EXAMPLE 2

Chewable Emulsion Shapes

The emulsion is prepared as in Example 1 and filled into an animal shape mould using a syringe. The shapes are then sealed into a blister pack.

EXAMPLE 3

Chewable Emulsion
Aqueous phase:
Gelatin: 10% wt.
Xylitol: 36% wt
Sorbitol: 14% wt.
Lemon flavour: 0.15% wt.
Yellow colour: 0.1% wt.
50% citric acid: 1% wt
Water: to 100% wt.

The gelatin is added to the water and allowed to swell for 30 min. The gelatin solution is then heated to 60° C. under continuous stirring for 45 min. The xylitol and sorbitol is then added to the solution and allowed to dissolve under stirring for 30-60 min. The acid, flavour and colour are then added while stirring. The solution is mixed for 30 min before stirring is stopped and the solution is left for 30 min. The resultant solution is degassed under vacuum to remove air bubbles.

Marine oil (e.g. commercially available fish liver oil) is mixed with 0.15% wt. lemon flavour.

The marine oil and the aqueous solution are emulsified in a weight ratio of 1:2 at 45-50° C. using an ultra turrax. When the emulsion is smooth, soft cores are produced by moulding and left to gel for 60 min at 22° C. The cores are dried to reduce the content of water to approximately 10% wt

EXAMPLE 4

Chewable Emulsion
Aqueous Phase:
Gelatin: 10% wt.
Xylitol: 36% wt
Sorbitol: 14% wt.
Lemon flavour: 0.15% wt.
Yellow colour: 0.1% wt.
50% citric acid: 1% wt
Water: to 100% wt.

The gelatin is added to the water and allowed to swell for 30 min. The gelatin solution is then heated to 60° C. under continuous stirring for 45 min. The xylitol and sorbitol is then added to the solution and allowed to dissolve under stirring for 30-60 min. The acid, flavour and colour are then added while stirring. The solution is mixed for 30 min before stirring is stopped and the solution is left for 30 min. The resultant solution is degassed under vacuum to remove air bubbles.

Olive oil (e.g. commercially available Ybarra oil) is mixed with 0.15% wt. lemon flavour.

The oil and the aqueous solution are emulsified in a weight ratio of 1:2 at 45-50° C. using an ultra turrax. When the emulsion is smooth, soft cores are produced by moulding and left to gel for 60 min at 22° C. The cores are dried to reduce the content of water to approximately 10% wt.

EXAMPLE 5

Chewable Emulsion
Aqueous Phase:
Gelatin: 10% wt.
Xylitol: 36% wt
Sorbitol: 14% wt.
Lemon flavour: 0.15% wt.
Yellow colour: 0.1% wt.
50% citric acid: 1% wt
Water: to 100% wt.

The gelatin is added to the water and allowed to swell for 30 min. The gelatin solution is then heated to 60° C. under continuous stirring for 45 min. The xylitol and sorbitol is then added to the solution and allowed to dissolve under stirring for 30-60 min. The acid, flavour and colour are then added while stirring. The solution is mixed for 30 min before stirring is stopped and the solution is left for 30 min. The resultant solution is degassed under vacuum to remove air bubbles.

Rapeseed oil (Landlord REMA 1000) is mixed with 0.15% wt. lemon flavour.

The oil and the aqueous solution are emulsified in a weight ratio of 1:2 at 45-50° C. using an ultra turrax. When the emulsion is smooth, soft cores are produced by moulding and left to gel for 60 min at 22° C. The cores are dried to reduce the content of water to approximately 10% wt.

EXAMPLE 6

Chewable Emulsion
Aqueous Phase:
Fish gelatin: 10% wt.
Kappa-carrageenan: 0.5% wt
Xylitol: 36% wt
Sorbitol: 14% wt.
Lemon flavour: 0.15% wt.
Yellow colour: 0.1% wt.
Water: to 100% wt.

The kappa-carrageenan and fish gelatin is added to the water and allowed to swell for 30 min. The mixture is then heated to 90° C. under continuous stirring for 45 min. The xylitol and sorbitol is then added to the solution and allowed to dissolve under stirring for 30-60 min at 70° C. The flavour and colour are then added while stirring. The solution is mixed for 30 min before stirring is stopped and the solution is left for 30 min. The resultant solution is degassed under vacuum to remove air bubbles.

Marine oil (e.g. commercially available fish liver oil) is mixed with 0.15% wt. lemon flavour.

The marine oil and the aqueous solution are emulsified in a weight ratio of 1:2 at 45-50° C. using an ultra turrax. When the emulsion is smooth, soft cores are produced by moulding and left to gel for 12 hours at 4° C. The cores are dried at room temperature to reduce the content of water to approximately 10% wt

EXAMPLE 7

Chewable Emulsion
Aqueous Phase:
Gellan: 0.5% wt
Xylitol: 36% wt
Sorbitol: 14% wt.
Water: to 100% wt.
CaCl2-solution: 15 mM in the water phase The gellan is added to the water and the mixture is then heated to 95° C. under continuous stirring for 30 min. The xylitol and sorbitol is then added to the solution and allowed to dissolve under stirring for 30-60 min at 70° C. The solution is mixed for 30 min before stirring is stopped and the solution is left for 30 min. The resultant solution is degassed under vacuum to remove air bubbles.

Marine oil (e.g. commercially available fish liver oil) is mixed with 0.15% wt. lemon flavour.

The marine oil and the aqueous solution are emulsified in a weight ratio of 1:2 at 60° C. using an ultra turrax. When the emulsion is smooth CaCl2 is added to a final concentration of 15 mM and soft cores are produced by moulding and left to gel for 180 min at 4° C. The cores are dried at room temperature to reduce the content of water to approximately 10% wt.

EXAMPLE 8

Chewable Emulsion
Aqueous Phase:
Gelatin: 7.5%
Xylitol: 36% wt
Sorbitol: 14% wt.
50% citric acid: 1% wt
Lemon flavour: 0.15% wt.
Yellow colour: 0.1% wt.
Water: to 100% wt.
Paracetamol: 125 mg/1.5 g emulsion The gelatin is added to the water and allowed to swell for 30 min. The gelatin solution is then heated to 60° C. under continuous stirring for 45 min. The acid, xylitol and sorbitol is then added to the solution and allowed to dissolve under stirring for 30-60 min. The flavour and colour are then added while stirring. The solution is mixed for 30 min before stirring is stopped and the solution is left for 30 min. The resultant solution is degassed under vacuum to remove air bubbles.

Olive oil is mixed with 0.15% wt. lemon flavour.

The olive oil and the aqueous solution are emulsified in a weight ratio of 1:2 at 60° C. using an ultra turrax. When the emulsion is smooth paracetamol powder is mixed into the emulsion with a ultra turrax and soft cores are produced by moulding and left to gel for 180 min at 200C. The cores are dried at room temperature to reduce the content of water to approximately 10% wt.

EXAMPLE 9

Chewable Emulsion
Aqueous Phase:
Na-alginate: 0.5% wt
Xylitol: 36% wt
Sorbitol: 14% wt.
Lemon flavour: 0.15% wt.
Yellow colour: 0.1% wt.
Water: to 100% wt.
GDL: 30 mM
$CaCO_3$: 15 mM The alginate is added to the water and dissolved under continuous stirring at room temperature for 6 hours. The xylitol and sorbitol is then added to the solution and allowed to dissolve under stirring for 30-60 min at 70° C. The solution is cooled to room temperature and flavour and colour is added. The resultant solution is degassed under vacuum to remove air bubbles.

Marine oil (e.g. commercially available fish liver oil) is mixed with 0.15% wt. lemon flavour.

The marine oil and the aqueous solution are emulsified in a weight ratio of 1:2 at room temperature using an ultra turrax. When the emulsion is smooth the $CaCO_3$ and GDL powders are added (one by one) and mixed into the emulsion by the ultra turrax. Soft cores are produced by moulding and left to gel for 24 hours at room temperature. The cores are dried at room temperature to reduce the content of water to approximately 10% wt

EXAMPLE 10

Chewable Emulsion
Aqueous Phase:
Na-alginate: 0.5% wt
Xylitol: 36% wt
Sorbitol: 14% wt.
Lemon flavour: 0.15% wt.
Yellow colour: 0.1% wt.
Water: to 100% wt.
Calsiumsulphate ($CaSO_4 \times 2H_2O$): 0.3%
Tetrasodiumpyrophosphate ($Na_4P_2O_7$): 0.03%

The alginate is added to the water and dissolved under continuous stirring at room temperature for 6 hours. The xylitol and sorbitol is then added to the solution and allowed to dissolve under stirring for 30-60 min at 70° C. The solution is cooled to room temperature and flavour and colour is added. The resultant solution is degassed under vacuum to remove air bubbles.

Marine oil (e.g. commercially available fish liver oil) is mixed with 0.15% wt. lemon flavour.

The marine oil and the aqueous solution are emulsified in a weight ratio of 1:2 at room temperature using an ultra turrax. When the emulsion is smooth the CaSO4 and tetrasodiumpyrophosphate powders are added (one by one) and mixed into the emulsion by the ultra turrax. Soft cores are produced by moulding and left to gel for 24 hours at room temperature. The cores are dried at room temperature to reduce the content of water to approximately 10% wt.

EXAMPLE 11

Chewable Emulsion
Aqueous Phase:
Gelatin: 10% wt.
Xylitol: 36% wt
Sorbitol: 14% wt.
Lemon flavour: 0.15% wt.
Yellow colour: 0.1% wt.
50% citric acid: 1% wt
Water: to 100% wt.
Vitamin C (ascorbic acid): 10 g The gelatin is added to the water and allowed to swell for 30 min. The gelatin solution is then heated to 70° C. under continuous stirring for 45 min. The xylitol and sorbitol is then added to the solution and allowed to dissolve under stirring for 30-60 min. The acid, flavour and colour are then added while stirring. The temperature is lowered to 50° C. and the vitamin C powder is added to the solution. The solution is mixed for 30 min before stirring is stopped and the solution is left for 30 min.

Marine oil (e.g. commercially available fish liver oil) is mixed with 0.15% wt. lemon flavour.

The marine oil and the aqueous solution are emulsified in a weight ratio of 1:2 at 40-45° C. using an ultra turrax. The resultant emulsion is degassed under vacuum to remove air bubbles. When the emulsion is smooth, soft cores are produced by moulding and left to gel for 60 min at 22° C. The cores are dried to reduce the content of water to approximately 10% wt.

EXAMPLE 12

Blister Packs

The emulsion cores of Examples 1, 2 and 4 to 11 are filled into plastic blister pack trays over which a plastic/metal foil laminate is heat sealed.

EXAMPLE 13

Chewable Strips

Before setting, the emulsions of Examples 1, 2 and 4 to 12 are extruded into strips which are then sealed into individual plastic/metal foil laminate envelopes.

What is claimed is:

1. An orally administrable chewable composition in unit dosage form comprising a chewable, set, oil-in-water emulsion, in which the aqueous phase is gelled and constitutes about 50% to 60% wt. of the unit dosage form and in which the unit dosage from comprises about 40% wt. of a fish oil, wherein said aqueous phase comprises gelatin in an amount of about 10% to 25% wt. of the aqueous phase, and wherein the unit dosage form has an overall dose unit weight of 0.25 to 3 g, and wherein the composition, upon chewing, remains free of bad odor and taste.

2. The composition as claimed in claim 1 wherein said aqueous phase comprises gelatin and carageenan.

3. The composition as claimed in claim 1 further comprising at least 1% wt. xylitol.

4. The composition as claimed in claim 1 further comprising a citrus flavor.

5. The composition as claimed in claim 1 wherein said aqueous phase comprises a water soluble vitamin.

6. The composition as claimed in claim 1 in animal, doll, vehicle, rod, strip or tube shape.

7. A package comprising an air-tight compartment containing one dose unit of a composition as claimed in claim 1.

8. The package as claimed in claim 7 in the form of a blister pack.

9. A method of treatment of a human by oral administration of an effective amount of an active agent in oil form or dissolved in an oil comprising administering said active agent in a chewable composition according to claim 1.

10. The method as claimed in claim 9 wherein said active agent is an analgesic.

11. The method as claimed in claim 9 wherein said active agent is a triglyceride.

12. The composition as claimed in claim 1, wherein said aqueous phase comprises gelatin in an amount of about 10% wt. of the aqueous phase.

* * * * *

UNITED STATES PATENT AND TRADEMARK OFFICE
CERTIFICATE OF CORRECTION

| | | |
|---|---|---|
| PATENT NO. | : 9,539,205 B2 | Page 1 of 1 |
| APPLICATION NO. | : 12/162339 | |
| DATED | : January 10, 2017 | |
| INVENTOR(S) | : Ingvild Haug et al. | |

It is certified that error appears in the above-identified patent and that said Letters Patent is hereby corrected as shown below:

On the Title Page

Immediately before Item (51), please insert the following header and data:
--Foreign Application Priority Data
Jan. 25, 2006 (GB) ..........................0601498.9--.

In the Claims

In Column 10 at Line 13, in Claim 1, change "from" to --form--.

Signed and Sealed this
Third Day of April, 2018

Andrei Iancu
*Director of the United States Patent and Trademark Office*